United States Patent [19]

Yoshioka et al.

[11] 4,283,333
[45] Aug. 11, 1981

[54] α-[4-OXOAZETIDIN-1-yl]-ACETIC ACID COMPOUNDS USEFUL AS INTERMEDIATES IN PREPARING 1-OXADETHIACEPHALOSPORINS

[75] Inventors: Mitsuru Yoshioka, Toyonaka; Yoshio Hamashima, Kyoto; Wataru Nagata, Nishinomiya, all of Japan

[73] Assignee: Shionogi & Co., Ltd., Osaka, Japan

[21] Appl. No.: 19,895

[22] Filed: Mar. 12, 1979

Related U.S. Application Data

[62] Division of Ser. No. 819,505, Jul. 26, 1977, abandoned.

[30] Foreign Application Priority Data

Jul. 28, 1976 [JP] Japan .................................. 51-90690

[51] Int. Cl.³ .................. C07D 705/08; C07D 405/14; C07D 405/12; C07D 401/12
[52] U.S. Cl. .......................... 260/239 A; 260/239.3 R; 260/245.4; 260/340.7; 260/340.9 R; 544/359; 546/208; 546/256; 546/275
[58] Field of Search ............ 260/239 A, 245.4, 340.7, 260/340.9 R; 546/275, 208, 256; 544/359, 239.3 R

[56] References Cited

PUBLICATIONS

Yoshioka et al., Chem. Abs., 88, 169941k, (1978).

*Primary Examiner*—Mark L. Berch
*Attorney, Agent, or Firm*—Wenderoth, Lind & Ponack

[57] ABSTRACT

Azetidine derivatives of the formula:

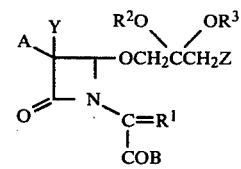

wherein A is amino or substituted amino; COB is carboxy or protected carboxy; $R^1$ is $=C(CH_3)_2$,

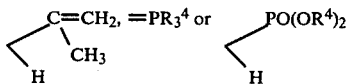

($R^4$ is alkyl, aryl or aralkyl); $OR^2$ and $OR^3$ independently or taken together with each other represent a ketal; Y is hydrogen or methoxy; Z is hydrogen or halogen, and a process for preparation thereof. Used as intermediates in the preparation of potent antimicrobials 1-oxadethiacephalosporins.

23 Claims, No Drawings

α-[4-OXOAZETIDIN-1-yL]-ACETIC ACID COMPOUNDS USEFUL AS INTERMEDIATES IN PREPARING 1-OXADETHIACEPHALOSPORINS

This is a division of application Ser. No. 819,505, filed July 26, 1977, now abandoned.

SUMMARY OF INVENTION

This invention relates to (1) compounds represented by the formula:

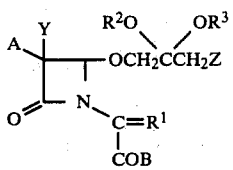

wherein A is amino or substituted amino; COB is carboxy or protected carboxy; $R^1$ is $=C(CH_3)_2$,

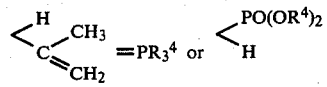

($R^4$ is alkyl, aryl or aralkyl); $OR^2$ and $OR^3$ independently or taken together represent a ketal; Y is hydrogen or methoxy; Z is hydrogen or halogen, and (2) a process for preparing compounds represented by the formula:

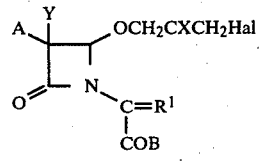

by halogenating compounds represented by the formula:

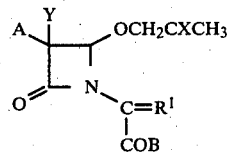

wherein A, COB, $R^1$ and Y are the same as mentioned above; Hal is halogen; X is oxo or

($OR^2$ and $OR^3$ are the same as mentioned above).

More particularly, it relates to reactions (2), (3) and (4) and compounds (III) and (IV) illustrated in the following reaction sequence.

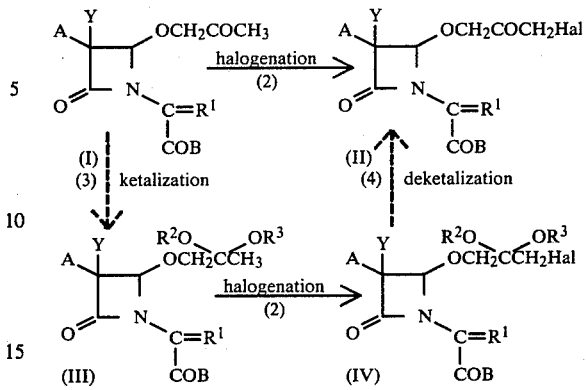

wherein A, COB, Hal, $R^1$, $OR^2$, $OR^3$ and Y are the same as mentioned above.

In other words, this invention relates to intermediates in the preparation of 1-oxadethiacephalosporins and processes for preparing them, which comprise (1) ketals (III) of methyl ketones (I) and ketals (IV) of halomethyl ketones (II); (2) a process for preparing halomethyl ketones (II) or their ketals (IV) on halogenation of methyl ketones (I) on their ketals (III); (3) a process for preparing ketals (III) on ketalization of methyl ketones (I); (4) a process for preparing halomethyl ketones (II) on deketalization of ketals (IV); and (5) a process for preparing halomethyl ketones (II) from methyl ketones (I) by carrying out the aforementioned processes (3), (2) and (4) successively.

1. Substituted-amino A

The substituted-amino A can be a side chain of natural or synthetic penicillins or cephalosporins, which is stable during the reaction, exemplified by an organic or inorganic acylamino, diacylamino, hydrocarbylamino, sulfenylamino, silylamino or acid addition salt of an amino group.

Representative of the acyl in the aforementioned acylamino include:

(1) ($C_1$-$C_{10}$)alkanoyls;
(2) ($C_1$-$C_5$)haloalkanoyls;
(3) azidoacetyls or cyanoacetyls;
(4) acyl groups of the formula: Ar—CQQ'—CO— wherein Q and Q' each are hydrogen or methyl; Ar is phenyl, dihydrophenyl, or monocyclic heteroaromatic group involving 1-4 nitrogen, oxygen and/or sulfur atoms, which may optionally be substituted by an inert group such as ($C_1$-$C_5$) alkyls, trifluoromethyl, cyano, aminomethyl, protected carboxymethylthio, hydroxy, ($C_1$-$C_3$)alkoxy, ($C_1$-$C_{10}$)acyloxy, chlorine, bromine, iodine, fluorine and nitro;
(5) 2-sydnon-3-acetyl or (4-pyridone-1-yl)acetyl;
(6) acyl groups of the formula: Ar—G—CQQ'—CO— wherein Ar, Q, and Q' are the same as mentioned above; G is oxygen atom or sulfur atom;
(7) acyl groups of the formula:

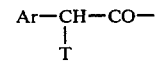

wherein Ar is the same as mentioned above; T is (i) hydroxy or ($C_1$-$C_{10}$)acyloxy; (ii) carboxy, ($C_2$-$C_7$)alkoxycarbonyl, ($C_8$-$C_{15}$)aralkoxycarbonyl, ($C_7$-$C_{12}$)aryloxycarbonyl, ($C_1$-$C_7$)alkanoyloxy, ($C_1$-$C_3$)alkoxy, cyano, carbamoyl; (iii) sulfo or $(C_1-C_7)$alkoxysulfonyl;

(8) acyl groups of the formula:

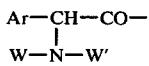

wherein Ar is the same as mentioned above; W and W' are respectively hydrogen or substituents on an amino group, e.g. $(C_2-C_7)$alkoxycarbonyl, $(C_3-C_{10})$cycloalkyl-$(C_2-C_3)$alkoxycarbonyl, $(C_5-C_8)$ cycloalkoxycarbonyl, $(C_1-C_4)$alkylsulfonyl-$(C_1-C_4)$alkoxycarbonyl, halo$(C_1-C_3)$alkoxycarbonyl, $(C_8-C_{15})$aralkoxycarbonyl, $(C_1-C_{10})$ alkanoyl or $(C_7-C_{15})$aroyl, which may optionally be substituted by inert groups such as hydroxy, $(C_1-C_{10})$alkanoyloxy, halogen, $(C_1-C_5)$alkyl, $(C_1-C_3)$hydroxyalkyl and trifluoromethyl; pyronecarbonyl, thiopyronecarbonyl, pyridonecarbonyl, carbamoyl, guanidinocarbonyl; substituted ureido carbonyls such as 3-methyl-2-oxoimidazolidin-1-ylcarbonyl and 3-methanesulfonyl-2-oxoimidazolidine-1-ylcarbonyl, substituted-amidoxalylcarbamoyls such as 4-methyl-2,3-dioxopiperazin-1-ylcarbonyl and 4-ethyl-2,3-dioxopiperazin-1-ylcarbonyl, substituted-thioureidocarbonyls corresponding to the aforementioned ureidocarbonyls; or W, W' and the nitrogen atom are, taken together, phthalimido, maleimido or enamino derived from enolic carbonyl compounds such as $(C_5-C_{10})$ acetoacetate, $(C_4-C_{10})$acetoacetamide, acetylacetone, acetoacetonitrile and 1,3-cyclopentanedione;

(9) acyl groups of the formula:

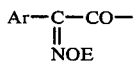

wherein Ar is the same as mentioned above; E is hydrogen or $(C_1-C_5)$alkyl;

(10) 5-aminoadipoyl; N-protected 5-aminoadipoyl, e.g. those N-protected by $(C_1-C_{10})$alkanoyl, $(C_1-C_{10})$aralkanoyl, $(C_2-C_{11})$aroyl, $(C_1-C_5)$haloalkanoyl, $(C_2-C_{10})$alkoxycarbonyl or the like; carboxy-protected 5-aminoadipoyl, e.g. those C-protected by $(C_1-C_5)$ alkyl, $(C_2-C_{21})$aralkyl, $(C_1-C_{10})$aryl, and the like; these protecting groups each may be substituted by $(C_1-C_5)$alkyl, $(C_1-C_5)$alkoxy, halogen, nitro or the like; and

(11) acyl groups of the formula: L—O—CO— wherein L is a readily removable $(C_1-C_{10})$hydrocarbon group which may be substituted, for example, t-butyl, 1,1-dimethylpropyl, cyclopropylmethyl, 1-methylcyclohexyl, isobutyl, 2-alkoxy-t-butyl, 2,2,2-trichloroethyl, benzyl, naphthyl, p-methoxybenzyl, pyridylmethyl, diphenylmethyl.

A may be diacylimido derived from $(C_4-C_{10})$dicarboxylic acids.

The substituted amino A includes amino substituted by $(C_1-C_{20})$hydrocarbyl or hydrocarbylidene (selected from t-butyl, trityl, methylidene, benzylidene, 1-halo-2-phenylethylidene, 1-alkoxy-2-phenylethylidene, 3,5-di-t-butyl-4-hydroxybenzylidene and o-hydroxybenzylidene, and $(C_2-C_{10})$organo silyl amino (e.g. trimethylsilylamino).

The amino A also includes groups which may be converted into amino or amido, such as azido, isocyanato, and isocyano.

Two amino substituents of A, taken together, may form a ring (e.g. 2,2-dimethyl-4-oxo-5-phenylimidazolidin-3-yl).

Reactive group A may be protected beforehand and, after termination of the reaction, deprotected in the conventional manner.

Most preferable group A is phenylacetamido and phenoxyacetamido.

2. Protected carboxy group COB

The group COB represents a carboxy group protected in the form of esters, amidos, acid halogenides, acid anhydrides, salts and the like.

Examples of the group B are oxygen functional groups such as $(C_1-C_{10})$alkoxy (e.g. methoxy, ethoxy, t-butoxy), $(C_7-C_{20})$ aralkoxy (e.g. benzyloxy, methoxybenzyloxy, nitrobenzyloxy, diphenylmethoxy, trityloxy), $(C_5-C_{15})$aryloxy (e.g. phenoxy, naphthyloxy), $(C_1-C_{12})$organo metallic oxy (e.g. trimethylstannyloxy, dimethylchlorosilyloxy, trimethylsilyloxy), $(C_1-C_{15})$organic or inorganic acyloxy, oxy of metal of I, II and III groups in the Periodic Table (e.g. sodiumoxy, potassiumoxy, magnesiumoxy), and $(C_1-C_{12})$ammoniumoxy; sulfur functional groups (e.g. groups which may form $(C_1-C_{12})$thiolester, thiocarboxy and the like; nitrogen functional groups, e.g. those which form amides such as N-$(C_1-C_5)$alkylamide, N,N-di$(C_1-C_5)$alkylamide, and amide with imidazole or phthalimide; groups which may form hydrazine or azide; or halogen atom (e.g. chlorine, bromine).

These groups, if possible, may involve hetero atoms such as oxygen, nitrogen and/or sulfur in the skeleton and may have unsaturation or substituents (e.g. nitrogen-, oxygen-, sulfur-, carbon-, phosphorus-functional group, halogen atoms).

Representative of COB are $(C_1-C_5)$haloalkylesters, $(C_2-C_5)$acylalkylesters, $(C_5-C_8)$arylesters, $(C_5-C_{20})$aralkylesters, esters of $(C_1-C_{12})$oxime, $(C_1-C_5)$-N-alkoxyamides, imides of dibasic acids, N,N'-di-$(C_3-C_5)$alkylhydrazides, salts of alkali or alkaline earth metals, salts of $(C_1-C_5)$alkylamines and other equivalent groups. (The aforementioned carbon number means that of B).

Preferable COB are esters of carboxylic acids (particularly, methyl-, t-butyl-, 2,2,2-trichloroethyl-, methanesulfonylethyl-, pivaroyloxymethyl-, phenacyl-, benzyl-, p-methoxybenzyl-, p-nitrobenzyl, benzhydryl-, indanyl-, benzaldoxime-, N,N-dimethylaminoethyl, and trimethylsilyl- esters), and salts of alkali metals or alkaline earth metals (e.g. lithium, sodium, potassium, magnesium, and other equivalent salts).

3. $R^1$ $R^1$ is isopropylidene, isopropenyl, $=PR^4_3$ or

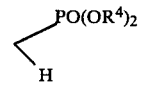

($R^4$ is alkyl such as methyl, ethyl, cyanoethyl, ethoxyethyl, propyl, chloropropyl, isobutyl, pentyl, cyclohexyl and octyl, aryl such as phenyl and tolyl or aralkyl such as benzyl and phenethyl). Since $R^1$ does not participate in the reaction, it can be varied widely, e.g. in possession of substituents.

4. OR², OR³

OR² and OR³ are independently or taken together ketal forming groups such as alkoxy (e.g. methoxy, ethoxy, propoxy, isobutoxy, pentyloxy, cyclohexyloxy, octyloxy), aralkoxy (e.g. benzyloxy, phenethyloxy, pyridylmethoxy), alkylenedioxy (e.g. ethylenedioxy, propylenedioxy, trimethylenedioxy), and aralkylenedioxy (e.g. phenylethylenedioxy, phenyltrimethylenedioxy, diphenylpropylenedioxy). OR² and OR³, since they are removed after termination of the reaction, can be varied widely, e.g. in possession of substituents, so far as the reaction is not obstructed.

5. Z, Hal

Z is hydrogen or halogen.
Hal is halogen such as chlorine, bromine and iodine.

6. Y

Y is hydrogen or methoxy.
Cephalosporins derived from methoxylated derivatives exhibit especially excellent antimicrobial action in many cases.

STARTING MATERIALS (i) Starting materials (I), for example, α-(2ξ-acetonyloxy-3β-acylamido-4-oxoazetidin-1-yl)-α-isopropylideneacetate, may be prepared by reacting already well-known α-(2ξ-chloro-3β-acylamido 4-oxoazetidin-1-yl)-α-isopropylideneacetate with propargyl alcohol in the presence of silver fluoroborate to yield α-(2ξ-propargyloxy-3β-acylamido-4-oxoazetidin-1-yl)-α-isopropylideneacetate and hydrating the latter in the presence of mercury salts.

(ii) The isopropylideneacetates thus prepared are subjected to cleavage reaction with ozone to yield α-(2ξ-acetonyloxy-3β-acylamido-4-oxoazetidin-1-yl)glyoxalates, which are reduced and halogenated to yield α-(2ξ-acetonyloxy-3β-acylamido-4-oxoazetidin-1-yl)-α-chloroacetate; the latter is heated in the presence of triethyl phosphite to yield the other starting materials, α-(2ξ-acetonyloxy-3β-acylamido-4-oxoazetidin-1-yl)-α-diethylphosphoroylacetates.

(iii) The other starting materials, α-(2ξ-acetonyloxy-3β-acylamido-4-oxoazetidin-1-yl)-α-triphenylphosphoranylideneacetates may be prepared from α-(2ξ-acetonyloxy-3β-acylamido-4-oxoazetidin-1-yl)-α-yl)-α-chloroacetates prepared in the manner as mentioned in (ii), on reaction with triphenylphosphine.

The remainder of (I) may be prepared in the conventional manners, for example, by modifying the aforementioned methods, the raw materials, reagents and the like or by modifying the desired portion of the aforementioned other starting materials (1).

The processes have been described in Japanese Patent Application Open to Public Inspection No. 49-133594.

PRIOR ARTS

Halogenation of acetonyloxy groups of α-(2ξ-acetonyloxy-3β-acylamido-2-oxoazetidin-1-yl)-acetates is not known yet. Halogenation usually takes place at the methyl and methylene groups of acetonyloxy group, but the location and influence on other reactive groups in the molecule have not yet been elucidated.

The halogenation of the corresponding acetonylthio derivatives is not known.

PREPARATION

(A) Halogenation (2)

The aforementioned halomethyl ketones (II) or their ketals (IV) are prepared from methyl ketones (I) or their ketals (III) on halogenation.

The halogenation is carried out as follows:

(i) the starting materials, methylketones (I) or their ketals (III) are dissolved in a solvent (such as hydrocarbon, halohydrocarbon, ether, ester, alcohol, carboxylic acid, amide or like solvent or their mixtures);

(ii) a halogenating agent (such as molecular halogens, cupric halogenides, mercury halogenides, molecular compounds of hydrohalogenic acids, aromatic bases and halogens, molecular compounds of phenyltrimethylammonium halogenides and halogens, N-haloamides, N-haloimides, esters of hypohalogenous acid, hypohalogenites and other halogenating agents) is added; and (iii) the reaction is conducted preferably at room temperature or under warming. Ordinarily, the reaction terminates within a period of 0.5–10 hours, but sometimes requires more than 20 hours at room temperature.

(iv) The preferable solvents are those which may participtate in ketalization, such as primary alcohols, glycols, and 1,3-diols. These solvents promote the reaction accompanied by ketalization of methylketone (I) in the presence of acids or halogenating agents in the reaction medium.

(v) Most preferable halogenating agents are cupric halogenides (e.g. cupric bromide), and molecular compounds of pyridinium hydrohalogenides and halogens (e.g. molecular compound of pyridine hydrobromide and bromine), by which the reaction proceeds mildly with formation of a minor quantity of by-product.

(vi) Preferable starting materials are ketals (III) of methyl ketones; in this case, the reaction proceeds rapidly with formation of very small quantity of by-product. The yield of halogenation other than through the ketals is 10–30%, whereas that through the ketals is 50–100%.

(vii) This reaction proceeds particularly smoothly under ketalizable conditions (e.g. in alcohol, in the presence of mineral acid or Lewis acid) to give the objective compounds in high yield.

(B) Ketalization (3)

Methylketones (I) are ketalized to yield ketals (II) of methylketones.

The ketalization is carried out as follows:

(i) Methylketone (I) is dissolved in a solvent (such as the alcohols halohydrocarbons, ethers, esters, amides or their mixtures containing a ketalizing agent, such as primary or secondary alcohols (e.g. methanol, ethanol, propanol, secondary butanol, benzyl alcohol), glycols (e.g. ethylene glycol, propylene glycol, phenylethylene glycol), diols (e.g. trimethylene glycol, 3-hydroxybutanol), ortho esters; or other ketalizing agents.

(ii) The reaction is conducted in the presence or absence of a catalyst (e.g. mineral acids; sulfonic acids; mineral acid salts with heavy metals, particularly cupric bromide, copper sulfate; other ketalization catalysts).

(iii) The reaction is conducted preferably at about −20° to 50° C.

The aforementioned halogenating agents may also serve as catalysts for ketalization.

(C) Deketalization (4)

Ketals (IV) of halomethylketones are deketalized to yield halomethylketones (II).

The deketalization may be carried out as follows:

(i) The ketals (IV) of halomethylketones are dissolved in an aqueous solvent (such as halohydrocarbon, ether, ester, amide, carboxylic acid, ketone or like solvents, or their mixtures).

(ii) The reaction is conducted in the presence of a catalyst (such as mineral acids, organic acids, e.g. sulfonic acids), (iii) at $-20°$ to $100°$ C. for 1 to 30 hours. The objective compounds are easily obtained.

(D) Successive Process

Each reaction described above may be carried out successively. For example, ketals (IV) may be prepared by halogenation immediately after the aforementioned ketalization of methylketones in a reaction vessel; the subsequent deketalization yields halomethylketones (II); deketalization is carried out after halogenation of ketals (III) of methylketones. When ketalization, halogenation, and deketalization are carried out successively, halomethylketones (II) are usually obtained from methylketones (I) in more than 95% overall yield. The yield is much higher than that of direct halogenation (10–30% yield) not through the ketal.

PRODUCTS AND USE

The products of each step may be purified in a conventional manner such as recrystallization, reprecipitation or chromatography, after removal of the unreacted starting materials reagents, by-products and solvents in a conventional manner such as extraction, washing, concentration and drying. It is natural to pay attention to deketalization on the action of acids during the treatment of ketals.

Halomethylketones (II) or their ketals (IV) are used as intermediates in the preparation of antimicrobial agents, 1-oxadethia-3-cephem-4-carboxylic acids.

For example, as shown in the accompanying reaction sequence, halomethylketones (II) are allowed to react with an aromatic heterocyclic thiol, e.g. 1-methyl-1H-tetrazol-5-ylthiol, to yield compounds (V), which are then cyclized under the Wittig reaction condition $R^1=P(C_6H_5)_3$ to yield antimicrobial agents, 1-oxa-1-dethia-3-cephem-4-carboxylic acid derivatives. For example, $7\beta[\alpha(3$-thienyl$)$-$\alpha$-carboxyacetamido]-$7\alpha$-methoxy-3-(1-methyltetrazol 5-yl)thiomethyl-1-oxa-1-dethia-3-cephem-4-carboxylic acid [VI: $A=\beta$-[$\alpha$-(3-thienyl)-$\alpha$-carboxyacetamido]; $Y=\alpha$-methoxy; $B=OH$-]is a potent antimicrobial against gram positive and negative bacteria, especially *Escherichia coli* and *Klebsiella pneumoniae*.

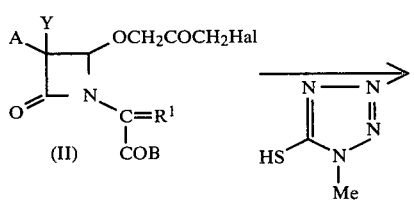

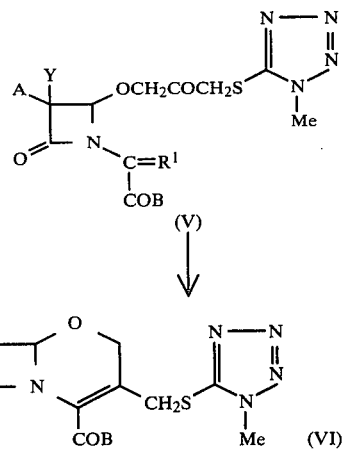

(wherein A, B, Y, $R^1$, and Hal are the same as mentioned above).

These compounds (VI) may be formulated with suitable excipients in the form of tablets or capsules for oral administration, vial or injection, and may be administered or injected to an adult human in single or divided doses containing from 100 mg to 1,000 mg of the active ingredient a day.

In order to prepare potent antimicrobial agents, it is appropriate to modify A, COB and Y in well-known manners.

The following examples are provided to further illustrate the products and processes of this invention.

EXAMPLE 1-1

(1) To a solution of 214 mg of benzyl $\alpha$-$(2\beta$-acetonyloxy-$3\beta$-phenylacetamido-4-oxoazetidin-1-yl)-$\alpha$-isopropylideneacetate in 5 ml of dry methanol is added 203 mg of cupric bromide, and the mixture allowed to stand at room temperature for 6 hours, poured into an aqeous sodium hydrogencarbonate solution and extracted with ethyl acetate. The extract is washed with water, dried over magnesium sulfate and evaporated under reduced pressure to yield 236 mg of benzyl $\alpha$-[$2\beta$-(2,2-dimethoxypropoxy)-$3\beta$-phenylacetamido 4-oxoazetidin-1-yl]-$\alpha$-isopropylidenacetate (100% yield).

IR: $\nu_{max}^{CHCl_3}$ 3470, 1790, 1740, 1695 cm$^{-1}$.

NMR: $\delta^{CDCl_3}$ 1.10s3H, 1.92s3H, 2.25s3H, 3.05s3H, 3.08s3H, 3.28s2H, 3.57s2H, 5.27+5.00ABq(12Hz)2H, 5.13d(5Hz)1H, 5.23dd(5;8Hz)1H, 6.22d(8Hz)1H, 7.20sl10H.

(2) To a solution of 213 mg of benzyl $\alpha$-$(2\beta$-acetonyloxy-$3\beta$-phenylacetamido-4-oxoazetidin-1-yl)-$\alpha$-isopropylideneacetate in 5 ml of dry methanol is added 320 mg of pyridine.hydrobromide- bromine complex, and the mixture stirred at 60° C. for 10 minutes to yield benzyl $\alpha$-[$2\beta$-(2,2-dimethoxypropoxy)-$3\beta$-phenylacetamido-4-oxoazetidin-1-yl-$\alpha$-isopropylidenacetate and benzyl $\alpha$-[$2\beta$-(2,2-dimethoxy-3-bromopropoxy)-$3\beta$-phenylacetamido-4-oxoazetidin-1-yl]$\alpha$-isopropylideneacetate.

EXAMPLE 1-2

(1) To a solution of 1.15 g of benzyl $\alpha$-$(2\beta$-acetonyloxy-$3\beta$-phenylacetamido-4-oxoazetidin-1-yl)-$\alpha$-isopropylideneacetate in 22 ml of dry ethanol is added 1.39 g of cupric bromide and 1.5 ml of triethyl orthoformate, and the mixture stirred under heating at 60° C. for 15 minutes to yield benzyl α-[2β-(2,2-diethoxypropoxy)-3β-phenylacetamido-4-oxoazetidin-1-yl]-α-isopropylideneacetate [TLC: Rf=80, C₆H₆+C₂H₅OCOCH₃ (1:1); precoated silica gel plate made by Merck Co.] Additionally, benzyl α-[2β-(2,2-diethoxy-3-bromopropoxy)-3β-phenylacetamido-4-oxoazetidin-1-yl]-α-isopropylideneacetate [TLC: Rf=0.90, C₆H₆+C₂H₅OCOCH₃ (1:1), precoated silica gel plate made by Merck Co.] is obtained as by-product.

EXAMPLE 1-3

To a solution of 0.54 g (1 mmole) of diphenylmethyl α-[2β-acetonyloxy-3β-phenylacetamido-4-oxoazetidin-1-yl)-α-isopropylideneacetate in 11 ml of dry methanol is added 0.56 g (2.5 mmoles) of cupric bromide, and the mixture stirred under heating at 40°–60° C. for 20 minutes to yield diphenylmethyl α-[2β-(2,2-dimethoxy-3-bromopropoxy)-3β-phenylacetamido-4-oxoazetidin-1-yl]-α-isopropylideneacetate and diphenylmethyl α-[2β-(2,2-dimethoxypropoxy)-3β-phenylacetamido-4-oxoazetidin-1-yl]-α-isopropylideneacetate.

EXAMPLE 1-4

To a solution of 0.54 g (1 mmole) of diphenylmethyl α-(2β-acetonyloxy-3β-phenylacetamido-4-oxoazetidin-1-yl)-α-isopropylideneacetate in 11 ml of dry ethanol is added 0.56 g (2.5 mmoles) of cupric bromide, and the mixture stirred under heating at 40°–60° C. for 10 minutes to yield diphenylmethyl α-[2β-(2,2-diethoxy-3-bromopropoxy)-3β-phenylacetamido-4-oxoazetidin-1-yl]-α-isopropylideneacetate and diphenylmethyl α-[2β-(2,2-diethoxypropoxy)-3β-phenylacetamido-4-oxoazetidin-1-yl]-α-isopropylideneacetate [TLC: Rf=0.55, C₆H₆+CH₃COOC₂H₅ (2:1) precoated silica gel plate made by Merck Co.].

EXAMPLE 1-5

The following compounds may be prepared in the same manner as mentioned in Examples 1-1 to 4.

(1) Methyl α-(2β-acetonyloxy-3β-phenoxyacetamido-4-oxoazetidin-1-yl)-α-isopropenylacetate is reacted with cupric chloride in dry ethanol at room temperature for 13 hours to yield methyl α-[2β-(2,2-diethoxypropoxy)-3β-phenoxyacetamido-4-oxoazetidin-1-yl]-α-isopropenylacetate.

(2) Similarly, 2,2,2-trichloroethyl α-(2β-acetonyloxy-3β-benzyloxycarbonamido-3α-methoxy-4-oxoazetidin-1-yl)-α-triphenylphosphoranylideneacetate is ketalized with propylene glycol and p-toluenesulfonic acid to yield 2,2,2-trichloroethyl α-[2β-(2,2-propylenedioxypropoxy)-3β-benzyloxycarbonamido-3α-methoxy-4-oxoazetidin-1-yl]-α-triphenylphosphoranylideneacetate.

(3) Benzyl α-[2β-acetonyloxy-3β-(α-phenyl-α-benzyloxycarbonylacetamido)-3α-methoxy-4-oxoazetidin-1-yl]-α-diethylphosphoroylacetate is reacted with cupric bromide in propanol at room temperature for 8 hours to yield benzyl α-[2β-(2,2-dipropoxypropoxy)-3β-(α-phenyl-α-benzyloxycarbonylacetamido)-3α-methoxy-4-oxoazetidin-1-yl]-α-diethylphosphoroylacetate.

EXAMPLE 2-1

(1) To a solution of 181 mg of benzyl α-(2β-acetonyloxy-3β-phenylacetamido-4-oxoazetidin-1-yl)-α-isopropylideneacetate dissolved in a mixture of 0.2 ml of tetrahydrofuran and 4 ml of t-butanol is added 640 mg of cupric bromide, and the mixture stirred at 75° C. for 1.5 hours. The reaction mixture is separated by thin layer chromatography on silica gel to yield benzyl α-[2β-(3-bromoacetonyloxy)-3β-phenylacetamido-4-oxoazetidin-1-yl]-α-isopropylideneacetate (25% yield).

(2) To a solution of 75 mg of benzyl α-(2β-acetonyloxy-3β-pheylacetamido-4-oxoazetidin-1-yl)-α-isopropylideneacetate in 1 ml of t-butanol is added one drop of 25% solution of hydrogen bromide in acetic acid and a solution of 26 mg of bromine in 0.32 ml of chloroform, and the mixture allowed to stand at room temperature overnight, then poured into water, and extracted with ethyl acetate. The extract is washed with water and dried over magnesium sulfate. The residue is chromatographed on a column of 5 g of silica gel containing 10% water, eluted with ethyl acetate-benzene, and evaporated to yield 13 mg of benzyl α-[2β-(3-bromoacetonyloxy)-3β-phenylacetamido-4-oxoazetidin-1-yl]-α-isopropylideneacetate (14.8% yield).

(3) To a solution of 139 mg (0.3 mmole) of benzyl α-(2β-acetonyloxy-3β-phenylacetamido-4-oxoazetidin-1-yl)-α-isopropylideneacetate in 1.3 ml of dry t-butanol and 0.2 ml of dry dichloroethane is added 192 mg (0.6 mmole) of pyridinium hydrobromide-bromine complex, and the mixture warmed at 45°–50° C. for 1 hour. Then, an additional 9 ml (0.13 mmole) of pyridinium hydrobromide-bromine complex is added, and the mixture heated for 1 hour. Separation by thin layer chromatography yields benzyl α-[2β-(3-bromoacetonyloxy)-3β-phenylacetamido-4-oxoazetidin-1-yl]-α-isopropylideneacetate (33% yield). The products, prepared in (1)–(3) described above, are identical and have the following constants.

IR: $\nu_{max}^{CHCL_3}$ 3420, 1780, 1730, 1685 cm⁻¹.

NMR: $\delta^{CDCl_3}$ 1.98s3H, 2.25s3H, 3.62s2H, 3.68s2H, 4.12s2H, 5.1–5.5m4H, 6.73d(7 Hz)1H, ca.7.4–10H.

EXAMPLE 2-2

(1) To a solution of 89 mg of benzyl α-[2β-(2,2-dimethoxypropoxy)-3β-phenylacetamido-4-oxoazetidin-1-yl]-α-isopropylideneacetate in 3 ml of methanol is added 85 mg of cupric bromide, and the mixture refluxed under heating for 4 hours. The reaction mixture is worked up, and the extract washed with water, dried, and evaporated. The residue is separated by thin layer chromatography to yield 49 mg of benzyl α-[2β-(2,2-dimethoxy-3-bromopropoxy)-3β-phenylacetamido-4-oxoazetidin-1-yl]-α-isopropylideneacetate (47.6% yield).

IR: $\nu_{max}^{CHCl_3}$ 3440, 1780, 1720, 1690 cm⁻¹.

NMR: $\delta^{CDCl_3}$ 1.97s3H, 2.25s3H, 3.13s6H, 3.23s2H, 3.42+3.73ABq(12 Hz) 2H, 3.63s2H, 5.03+5.66ABq(12 Hz)2H, 5.27d(5 Hz)1H, 5.33dd(5;8 Hz)1H, 6.23d(8 Hz)1H, 7.33s5H, 7.40s5H.

(2) To a solution of 97 mg of benzyl α-[2β-(2,2-dimethoxypropoxy)-3β-phenylacetamido-4-oxoazetidin-1-yl]-α-isopropylideneacetate in 2 ml of dry methanol is added 140 mg of pyridinium hydrobromide-bromide complex, and the mixture refluxed under heating for 30 minutes, then poured into water, and then extracted with ethyl acetate. The extract is washed with water, dried over magnesium sulfate, and then evaporated. The residue (132 mg) is chromatographed on a column of 4.5 g of silica gel containing 10% water, and eluted with 15% ethyl acetate-benzene. The eluate is concentrated to yield 56 mg of benzyl α-[2β-(2,2-dimethoxy-3-bromopropoxy)-3β-phenylacetamido-4-oxoazetidin-1-yl]-α-isopropylideneacetate (50.0% yield). This product is identical with that prepared in (1) described above.

EXAMPLE 2-3

The reaction mixture of Example 1-2(3) is further heated with stirring, and after termination of the bromination, cooled to room temperature. The mixture is then poured into 5% aqueous sodium hydrogencarbonate solution, the precipitate removed off by filtration and the filtrate extracted with ethyl acetate. The extract is washed with an aqueous sodium chloride solution, dried over sodium sulfate and evaporated under reduced pressure to yield 1.62 g of crude benzyl α-[2β-(2,2-diethoxy-3-bromopropoxy)-3β-phenylacetamido-4-oxoazetidin-1-yl]-α-isopropylideneacetate (106% yield).

IR: $\nu_{max}^{CHDl_3}$ 3420, 1775, 1720, 1680 cm$^{-1}$.

NMR: $\delta^{CDCl_3}$ 1.13t(7 Hz)6H, 1.98s3H, 2.25s3H, 3.2–3.7 m10H, 5.0–5.5m4H, 6.52d(8 Hz)1H, ca.7.4–10H.

EXAMPLE 2-4

The reaction mixture of Example 1-3 is further heated with stirring, and after termination of the bromination, poured into 5% aqueous sodium hydrogencarbonate solution. The resulting insoluble material (cuprous bromide) is filtered off, and the filtrate extracted with ethyl acetate. The extract is washed with water, dried and then evaporated to yield diphenylmethyl α-[2β-(2,2-dimethoxy-3-bromopropoxy)-3β-phenylacetamido-4-oxo-azetidin-1-yl]-α-isopropylideneacetate as crystals.

EXAMPLE 2-5

The reaction mixture of Example 1-4 is further heated with stirring, and after termination of the bromination, poured into 5% aqueous sodium hydrogencarbonate solution. The resulting insoluble material (cuprous bromide) is filtered off, and the filtrate extracted with ethyl acetate. The extract is washed with water, dried and evaporated to yield diphenylmethyl α-[2β-(2,2-diethoxy-3-bromopropoxy)-3β-phenylacetamido-4-oxoazetidin-1-yl]-α-isopropylideneacetate (64.6% yield).

NMR: $\delta^{CDCl_3}$ 1.05t(7 Hz)6H, 1.93s3H, 2.18s3H, 3.0–3.8m8H, 3.57s2H, 5.20d(4 Hz)1H, 5.37dd(4;8 Hz)1H, 6.32d(8 Hz)1H, 6.95s1H, ca.7.3m15H.

EXAMPLE 2-6

The following compounds may be prepared in the same manner as in Examples 2-1 to 5.

(1) The reaction mixture of Example 1-5(1) is refluxed under heating for 6 hours to yield methyl α-[2β-(3-chloro-2,2-diethoxypropoxy)-3β-phenoxyacetamido-4-oxoazetidin-1-yl]-α-isopropenylacetate.

(2) A solution of 2,2,2-trichloroethyl α-[2β-(2,2-propylenedioxypropoxy)-3β-benzyloxycarbonylamino-3α-methoxy-4-oxoazetidin-1-yl]-α-triphenylphosphoranylideneacetate in dioxane is reacted with cupric bromide at 60° C. for 5 hours to yield 2,2,2-trichloroethyl α-[2β-(3-bromo-2,2-propylenedioxypropoxy)-3β-benzyloxycarbonylamino-3α-methoxy-4-oxoazetidin-1yl]-α-triphenylphosphoranylideneacetate.

(3) The reaction mixture of Example 1-5(3) is refluxed under heating for 6 hours to yield benzyl α-[2β-(3-bromo-2,2-dipropoxypropoxy)-3β-(α-phenyl-α-benzyloxycarbonylacetamido)-3α-methoxy-4-oxoazetidin-1-yl]-α-diethylphosphoroylacetate.

EXAMPLE 3-1

To a solution of 12 mg of benzyl α-[2β-(2,2-dimethoxy-3-bromopropoxy)-3β-phenylacetamido-4-oxoazetidin-1-yl]-α-isopropylideneacetate in 1 ml of acetone is added 0.2 ml of water and one drop of 60% perchloric acid, and the mixture kept at room temperature for 3 hours and then at 70° C. for 30 minutes. The mixture is poured into water, and extracted with ethyl acetate. The extract is washed with water, dried over magnesium sulfate and evaporated to yield 9 mg of residue, which is separated by thin layer chromatography on silica gel to yield benzyl α-[2β-(3-bromoacetonyloxy)-3β-phenylacetamido-4-oxoazetidin-1-yl]-α-isopropylideneacetate (50% yield). The product is identical with that prepared in Example 2-1.

EXAMPLE 3-2

To a solution of 1.62 g of benzyl α-[2β-(2,2-diethoxy-3-bromopropoxy)-3β-phenylacetamido-4-oxoazetidin-1-yl]-α-isopropylideneacetate in 50 ml of acetone is added 15 ml of water and 7 ml of 30% perchloric acid, and the mixture stirred at 50° C. for 4⅔ hours. Acetone is evaporated under reduced pressure, and the residue is extracted with ethyl acetate. The extract is washed with 5% aqueous sodium hydrogencarbonate solution, an aqueous sodium chloride solution and then water, dried over sodium sulfate, and evaporated to yield 1.26 g of benzyl α-(2β-bromoacetonyloxy-3-phenylacetamido-4-oxoazetidin-1-yl)-α-isopropylideneacetate as crude crystals (93.6% yield). This product is identical with that prepared in Example 2-1.

EXAMPLE 3-3

To diphenylmethyl α-[2β-(2,2-dimethoxy-3-bromopropoxy-3-phenylacetamido-4-oxoazetidin-1-yl]-α-isopropylideneacetate is added acetone, water and 30% perchloric acid, and the mixture stirred at 50° C. for 6 hours. Acetone is evaporated and the residue is extracted with ethyl acetate. The extract is washed with an aqueous sodium hydrogencarbonate solution and water, dried, and evaporated to yield diphenylmethyl α-[2β-(3-bromoacetonyloxy)-3-phenylacetamido-4-oxoazetidin-1-yl]-α-isopropylideneacetate. The product is identical with that prepared in Example 3-4.

EXAMPLE 3-4

To a solution of 0.123 g (0.18 mmole) of diphenylmethyl α-[2β-(2,2-diethoxy-3-bromopropoxy-3β-phenylacetamido-4-oxoazetidin-1-yl]-α-isopropylideneacetate in 3.6 ml of acetone is added 1.2 ml of water and 0.6 ml of 30% perchloric acid, and the mixture stirred at 50° C. for 6 hours. Acetone is evaporated and the residue is extracted with ethyl acetate. The ethyl acetate layer is washed with an aqueous sodium hydrogencarbonate solution and then water, dried and evaporated to yield 0.95 g of diphenylmethyl α-[2β-(3-bromoacetonyloxy)-3-phenylacetamido-4-oxoazetidin-1-yl]-α-isopropylideneacetate (85.2% yield).

IR: $\nu_{max}^{CHCl_3}$ 3430, 1780, 1730, 1690 cm$^{-1}$. NMR: $\delta^{CDCl_3}$ 1.97s3H, 2.25s3H, 3.60s4H, 4.02s2H, 5.12d(4 Hz)1H, 5.30dd(4;8 Hz)1H, 6.72d(8 Hz)1H, 6.97s1H, 7.3m15H.

EXAMPLE 3-5

The following compounds may be prepared in the same manner as in Example 3-1 to 4.

(1) Methyl `α-[2β-(3-chloro-2,2-diethoxypropoxy)-3β-phenoxyacetamido-4-oxoazetidin-1-yl]-α-isopropenylacetate is hydrolyzed with perchloric acid in an aqueous acetone to yield methyl α-[2β-(3-chloroacetonyloxy)-3β-phenylacetamido-4-oxoazetidin-1-yl]-α-isopropenylacetate.

(2) A solution of 2,2,2-trichloroethyl α-[2β-(3-bromo-2,2-propylenedioxypropoxy)-3β-benzyloxycarbonylamino-3α-methoxy-4-oxoazetidin-1-yl]-α-triphenylphosphoranylideneacetate in 50% formic acid is heated with toluenesulfonic acid at 80° C. for 2 hours to yield 2,2,2-trichloroethyl α-[2β-(3-bromoacetonyloxy)-3β-benzyloxycarbonylamino-3α-methoxy-4-oxoazetidin-1-yl]-α-triphenylphosphoranylideneacetate.

(3) Benzyl α-[2β-(3-bromo-2,2-dipropoxypropoxy)-3β-(α-phenyl-α-benzyloxycarbonylacetamido)-3α-methoxy-4-oxoazetidin-1-yl]-α-diethylphosphoroylacetate is hydrolyzed with perchloric acid in an aqueous acetone to yield benzyl α-[2β-(3-bromoacetonyloxy)-3β-(α-phenyl-α-benzyloxycarbonylacetamido)-3α-methoxy-4-oxoazetidin-1-yl]-α-diethylphosphoroylacetate.

We claim:
1. A compound of the formula:

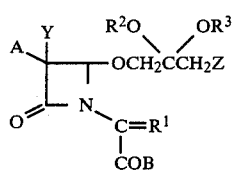

wherein A is amino,
acrylamino selected from the group consisting of
(1) $C_1$-$C_{10}$ alkanoylamino,
(2) $C_1$-$C_5$ haloalkanoylamino,
(3) azidoacetamido,
(4) cyanoacetamido,
(5) acylamino of the formula Ar—CQQ'—CONH—, wherein Q and Q' each are hydrogen or methyl, Ar is phenyl or dihydrophenyl, which phenyl and dihydrophenyl may be monosubstituted by $C_1$-$C_5$ alkyl, trifluoromethyl, cyano, aminomethyl, protected carboxymethylthio, hydroxy, $C_1$-$C_3$ alkoxy, $C_1$-$C_{10}$ alkanoyloxy, chlorine, bromine, iodine, fluorine, or nitro,
(6) 2-sydnon-3-acetamido,
(7) (4-pyridon-1-yl)-acetamido,
(8) acylamino of the formula Ar—G—CQQ'—CONH—, wherein Ar, Q, and Q' are the same as defined above and G is oxygen or sulfur,
(9) acylamino of the formula

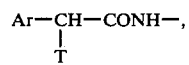

wherein Ar is the same as defined above and T is hydroxy, carboxy, $C_2$-$C_7$ alkoxycarbonyl, $C_8$-$C_{15}$ aralkoxycarbonyl, $C_7$-$C_{12}$ aryloxycarbonyl, $C_1$-$C_7$ alkanoyloxy, $C_1$-$C_3$ alkoxy, cyano, carbamoyl, sulfo or $C_1$-$C_7$ alkoxysulfonyl,
(10) acylamino of the formula

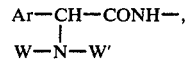

wherein Ar is the same as defined above and W and W' are, respectively, (i) hydrogen, (ii) $C_2$-$C_7$ alkoxycarbonyl, (iii) $C_3$-$C_{10}$ cycloalkyl-($C_2$-$C_3$)alkoxycarbonyl, (iv) $C_5$-$C_8$ cycloalkoxycarbonyl, (v) $C_1$-$C_4$ alkylsulfonyl-($C_1$-$C_4$)alkoxycarbonyl, (vi) halo($C_1$-$C_3$)alkoxycarbonyl, (vii) $C_8$-$C_{15}$ aralkoxycarbonyl, (viii) $C_1$-$C_{10}$ alkanoyl or (ix) $C_7$-$C_{15}$ aroyl, which groups (ii) through (ix) are unsubstituted or monosubstituted by hydroxy, $C_1$-$C_{10}$ alkanoyloxy, halogen, $C_1$-$C_5$ alkyl, $C_1$-$C_3$ hydroxyalkyl or trifluoromethyl, (x) pyronecarbonyl, (xi) thiopyronecarbonyl, (xii) pyridonecarbonyl, (xiii) carbamoyl, (xiv) guanidinocarbonyl, (xv) 3-methyl-2-oxoimidazolidin-1-ylcarbonyl, (xvi) 3-methanesulfonyl-2-oxoimidazolidin-1-ylcarbonyl, (xvii) 4-methyl-2,3-dioxopiperazin-1-ylcarbonyl or (xviii) 4-ethyl-2,3-dioxopiperazin-1-ylcarbonyl, or W and W', together with the nitrogen atom to which they are attached, represent phthalimido, maleimido or an enamino of the formula

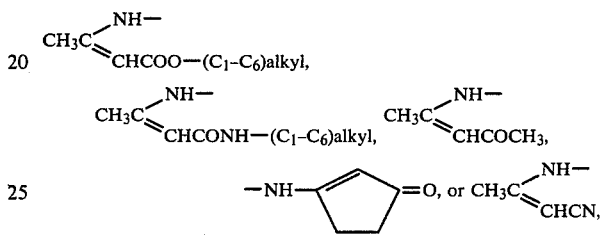

(11) acylamino of the formula

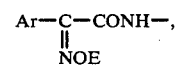

wherein Ar is the same as defined above and E is hydrogen or $C_1$-$C_5$ alkyl,
(12) 5-aminoadipoylamino,
(13) N-protected 5-aminoadipoylamino,
(14) carboxy-protected 5-aminoadipoylamino, and
(15) acylamino of the formula L—O—CONH—, wherein L is t-butyl, 1,1-dimethylpropyl, cyclopropylmethyl, 1-methylcyclohexyl, isobutyl, 2-alkoxy-t-butyl, 2,2,2-trichloroethyl, benzyl, naphthyl, p-methoxybenzyl, pyridylmethyl or diphenylmethyl,
diacylamino of the formula

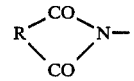

wherein R is a noncyclic $C_2$-$C_8$ hydrocarbon radical, amino substituted by t-butyl, trityl, methylidene, benzylidene, 1-halo-2-phenylethylidene, 1-alkoxy-2-phenylethylidene, 3,5-di-t-butyl-4-hydroxybenzylidene, o-hydroxybenzylidene or trimethylsilyl, or a group selected from azido, isocyanato and isocyano; COB is carboxy or protected carboxy; $R^1$ is $=C(CH_3)_2$,

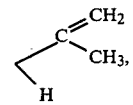

$=PR^4_3$ or

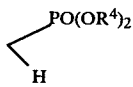

wherein $R^4$ is alkyl, monocyclic aryl or monocyclic aralkyl;

$OR^2$ and $OR^3$, independently of each other, represent methoxy, ethoxy, propoxy, isobutoxy, pentyloxy, cyclohexyloxy, octyloxy, benzyloxy, phenethyloxy or pyridylmethoxy, or $OR^2$ and $OR^3$, taken together, represent ethylenedioxy, propylenedioxy, trimethylenedioxy, phenylethylenedioxy, phenyltrimethylenedioxy or diphenylpropylenedioxy;

Y is hydrogen or methoxy; and

Z is hydrogen or halogen.

2. A compound claimed in claim 1, wherein $R^1$ is isopropylidene.

3. A compound claimed in claim 1, wherein $R^1$ is

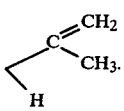

4. A compound claimed in claim 1, wherein $R^1$ is triarylphosphoranylidene.

5. A compound claimed in claim 1, wherein $R^1$ is dialkylphosphoroyl.

6. A compound claimed in claim 1, wherein B is $C_7$–$C_{20}$ aralkoxy.

7. A compound claimed in claim 1, wherein B is 2,2,2-trichloroethoxy.

8. A compound claimed in claim 1, wherein $OR^2$ and $OR^3$ are independently methoxy, ethoxy, propoxy, isobutoxy, pentyloxy or cyclohexyloxy.

9. A compound claimed in claim 1, wherein $OR^2$ and $OR^3$, taken together, represent ethylenedioxy, propylenedioxy or trimethylenedioxy.

10. A compound claimed in claim 1, namely benzyl α-[2β-(2,2-dimethoxypropoxy)-3β-phenylacetamido-4-oxoazetidin-1-yl]-α-isopropylideneacetate.

11. A compound claimed in claim 1, namely benzyl α-[2β-(2,2-dimethoxy-3-bromopropoxy)-3β-phenylacetamido-4-oxoazetidin-1-yl]-α-isopropylideneacetate.

12. A compound claimed in claim 1, namely benzyl α-[2β-(2,2-diethoxypropoxy)-3β-phenylacetamido-4-oxoacetidin-1-yl]-α-isopropylideneacetate.

13. A compound claimed in claim 1, namely benzyl α-[2β-(2,2-diethoxy-3-bromopropoxy)-3β-phenylacetamido-4-oxoazetidin-1-yl]-α-isopropylideneacetate.

14. A compound claimed in claim 1, namely diphenylmethyl α-[2β-(2,2-dimethoxy-3-bromopropoxy)-3β-phenylacetamido-4-oxo-azetidin-1-yl]-α-isopropylideneacetate.

15. A compound claimed in claim 1, namely diphenylmethyl α-[2β-(2,2-dimethoxypropoxy)-3β-phenylacetamido-4-oxoazetidin-1-yl]-α-isopropylideneacetate.

16. A compound claimed in claim 1, namely diphenylmethyl α-[2β-(2,2-diethoxy-3-bromopropoxy)-3β-phenylacetamido-4-oxoazetidin-1-yl]-α-isopropylideneacetate.

17. A compound claimed in claim 1, namely diphenylmethyl α-[2β-(2,2-diethoxypropoxy)-3β-phenylacetamido-4-oxoazetidin-1-yl]-α-isopropylideneacetate.

18. A compound claimed in claim 1, namely methyl α-[2β-(2,2-diethoxypropoxy)-3β-phenoxyacetamido-4-oxoazetidin--yl]-α-isopropenylacetate.

19. A compound claimed in claim 1, namely 2,2,2-trichloroethyl α-[2β-(2,2-propylenedioxypropoxy)-3β-benzyloxycarbonamido-3α-methoxy-4-oxoazetidin-1-yl]-α-triphenylphosphoranylideneacetate.

20. A compound claimed in claim 1, namely benzyl α-[2β-(2,2-dipropoxypropoxy)-3β-(α-phenyl-α-benzyloxycarbonylacetamido)-3α-methoxy-4-oxoazetidin-1-yl]-α-diethylphosphoroylacetate.

21. A compound claimed in claim 1, namely methyl α-[2β-(3-chloro-2,2-diethoxypropoxy)-3β-phenoxyacetamido-4-oxoazetidin-1-yl]-α-isopropenylacetate.

22. A compound claimed in claim 1, namely 2,2,2-trichloroethyl α-[2β-(3-bromo-2,2-propylenedioxypropoxy)-3β-benzyloxycarbonylamino-3α-methoxy-4-oxoazetidin-1-yl]-α-triphenylphosphoranylideneacetate.

23. A compound claimed in claim 1, wherein $R^4$ is methyl, ethyl, cyanoethyl, ethoxyethyl, propyl, chloropropyl, isobutyl, pentyl, cyclohexyl, octyl, phenyl, tolyl, benzyl or phenethyl.

* * * * *